US011135290B2

(12) United States Patent
Stahl et al.

(10) Patent No.: US 11,135,290 B2
(45) Date of Patent: Oct. 5, 2021

(54) FUCOSYLLACTOSE AS BREAST MILK IDENTICAL NON-DIGESTIBLE OLIGOSACCHARIDE WITH NEW FUNCTIONAL BENEFIT

(71) Applicant: N.V. Nutricia, Zoetermeer (NL)

(72) Inventors: Bernd Stahl, Utrecht (NL); Alma Jildou Nauta, Utrecht (NL); Johan Garssen, Utrecht (NL); Eric Samain, Gieres (FR); Sophie Drouillard, Claix (FR)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 16/750,565

(22) Filed: Jan. 23, 2020

(65) Prior Publication Data

US 2020/0155672 A1 May 21, 2020

Related U.S. Application Data

(63) Continuation of application No. 15/866,667, filed on Jan. 10, 2018, now Pat. No. 10,588,965, which is a continuation of application No. 14/869,436, filed on Sep. 29, 2015, now abandoned, which is a continuation of application No. 13/383,822, filed as application No. PCT/NL2010/050447 on Jul. 12, 2010, now abandoned.

(60) Provisional application No. 61/256,453, filed on Oct. 30, 2009.

(30) Foreign Application Priority Data

Jul. 15, 2009 (EP) .................................. 09165485

(51) Int. Cl.
| | | |
|---|---|---|
| A61K 31/702 | (2006.01) | |
| A61P 31/12 | (2006.01) | |
| A61P 37/04 | (2006.01) | |
| A61K 39/39 | (2006.01) | |
| A23L 29/30 | (2016.01) | |
| A23L 33/00 | (2016.01) | |
| A23L 33/10 | (2016.01) | |
| A61K 31/7032 | (2006.01) | |
| A23L 33/125 | (2016.01) | |
| A23L 5/00 | (2016.01) | |
| A61K 39/00 | (2006.01) | |

(52) U.S. Cl.
CPC ............. *A61K 39/39* (2013.01); *A23L 29/30* (2016.08); *A23L 33/10* (2016.08); *A23L 33/40* (2016.08); *A61K 31/702* (2013.01); *A61K 31/7032* (2013.01); *A61P 31/12* (2018.01); *A61P 37/04* (2018.01); *A23L 5/00* (2016.08); *A23L 33/125* (2016.08); *A23V 2002/00* (2013.01); *A61K 2039/55* (2013.01); *A61K 2039/572* (2013.01)

(58) Field of Classification Search
None
See application file for complete search history.

(56) References Cited

U.S. PATENT DOCUMENTS

| | | |
|---|---|---|
| 5,002,759 A | 3/1991 | Gaffar et al. |
| 6,576,251 B1 | 6/2003 | Stahl et al. |
| 8,591,919 B2 | 11/2013 | Stahl |
| 9,566,291 B2 | 2/2017 | Boehm et al. |
| 10,420,784 B2 | 9/2019 | Stahl et al. |
| 2002/0019991 A1 | 2/2002 | Prieto et al. |
| 2007/0274983 A1 | 11/2007 | Kluijtmans et al. |
| 2007/0275881 A1 | 11/2007 | Morrow et al. |
| 2008/0124323 A1 | 5/2008 | Boehm et al. |
| 2008/0145838 A1 | 6/2008 | Suda et al. |
| 2009/0035813 A1* | 2/2009 | Sprenger ................ A23L 29/30 435/68.1 |
| 2009/0221486 A1* | 9/2009 | Schmitt ................... A23L 33/10 514/6.9 |
| 2012/0177691 A1 | 7/2012 | Stahl et al. |
| 2012/0178674 A1 | 7/2012 | Stahl et al. |
| 2015/0031645 A1 | 1/2015 | Buck et al. |
| 2016/0316808 A1 | 11/2016 | Destaillats et al. |
| 2016/0354395 A1 | 12/2016 | Contractor et al. |

FOREIGN PATENT DOCUMENTS

| | | |
|---|---|---|
| EP | 1 105 002 B1 | 6/2001 |
| EP | 1 105 002 B2 | 6/2001 |
| EP | 1 597 978 A1 | 11/2005 |
| EP | 1 629 850 A1 | 3/2006 |
| EP | 1 629 850 B2 | 3/2006 |
| EP | 1 629 850 B1 | 5/2007 |
| EP | 2 072 052 A1 | 6/2009 |
| EP | 2 662 084 A1 | 11/2013 |
| EP | 2 813 230 A1 | 12/2014 |
| WO | WO-99/11773 A1 | 3/1999 |
| WO | WO-99/56754 A1 | 11/1999 |
| WO | WO-00/08948 A2 | 2/2000 |
| WO | WO-01/64225 A1 | 9/2001 |
| WO | WO-2005/039319 A2 | 5/2005 |

(Continued)

OTHER PUBLICATIONS

Armbrust et al., "Norovirus infections in preterm infants: wide variety of clinical courses" BMC research notes vol. 2 No. 96 pp. 1-6 (Year: 2009).*
Malloy et al., "Impact of Cesarean Section on Intermediate and Late Preterm Births: United States, 2000-2003" BIRTH vol. 36 No. 1 pp. 26-33 (Year: 2009).*
Verboon et al., "Clinical and Epidemiologic Characteristics of Viral Infections in a Neonatal Intensive Care Unit During a 12-Year Period" THe Pediatric Infectious Disease Journal vol. 24 No. 10 pp. 901-904 (Year: 2005).*
Laucirica et al., "Milk Oligosaccharides Inhibit Human Rotavirus Infectivity in MA104 Cells" The Journal of Nutrition vol. 147 pp. 1709-1714 (Year: 2017).*

(Continued)

*Primary Examiner* — Eric Olson
(74) *Attorney, Agent, or Firm* — Foley & Lardner LLP

(57) ABSTRACT

The invention concerns nutritional compositions with fucosyllactose for use in stimulation of NK cells. The composition is suitable for infants.

11 Claims, No Drawings

(56) References Cited

FOREIGN PATENT DOCUMENTS

| | | |
|---|---|---|
| WO | WO-2005/039597 A2 | 5/2005 |
| WO | WO-2005/055944 A2 | 6/2005 |
| WO | WO-2007/010084 A2 | 1/2007 |
| WO | WO-2007/067053 A1 | 6/2007 |
| WO | WO-2007/105945 A2 | 9/2007 |
| WO | WO-2007/114683 A1 | 10/2007 |
| WO | WO-2009/065905 A2 | 5/2009 |
| WO | WO-2009/077352 A1 | 6/2009 |
| WO | WO-2011/008086 A1 | 1/2011 |
| WO | WO-2011/008087 A1 | 1/2011 |
| WO | WO-2015/071391 A1 | 5/2015 |

OTHER PUBLICATIONS

Morrow et al., "Human Milk Oligosaccharides Are Associated With Protection Against Diarrhea in Breast-Fed Infants" J Pediatr vol. 145 pp. 297-303 (Year: 2004).*

Chen et al., "Effect of Human Milk Oligosaccharides on Rotavirus Infectivity in MA104 Cells" FASEB Journal vol. 25 Issue S1 p. 584.18 abstract (Year: 2011).*

"Annex E: In vitro lactate production upon fermentation of different ratio's of galacto-oligosaccharides and inulin by infant's faeces", Appeal proceedings of EP1105002 (E17b), filed with letter of patentee on Dec. 3, 2008 (2 pages).

"Bioprocesses and Biotechnology for Functional Foods and Nutraceuticals", Edited by Jean-Richard Neeser and J. Bruce German, 2004, pp. 103-105 (5 pages).

"Childhood Vaccine Schedule", NIH Medline Plus, Spring 2008, retrieved Apr. 10, 2013 from URL: http://www.nlm.nih.gov/medlineplus/magazine/issues/spring08/articles/spring08pg7.html (2 page).

"Dog Vaccination Schedule", Dog Care: Vaccination Schedule, Nov. 29, 2008, retrieved Apr. 10, 2013 from URL: http://samanjith.blogspot.com/2008/11/dog-vaccination-schedule.html (5 pages).

"Milk Facts: Nutritional Components in Milk", MilkFacts.info, retrieved Oct. 23, 2012 from URL: http://www.milkfacts.info/Nutrition%20Facts/Nutritional%20Components.htm (7 pages).

"Prebiotics in Infant Nutrition", edited by Sharon Donovan, Glenn Gibson, and David Newburg, Mead Johnson Nutrition, 2009, pp. 1-37 (21 pages).

"The Condensed Chemical Dictionary" Revised by Gessner G. Hawley, 10th ed., 1981, pp. 759 (3 pages).

Acknowledgement of Receipt and Letter in reply to communication under Rule 161(1) EPC in European Application No. 10734842.7 dated Sep. 10, 2012 (4 pages).

Benyacoub et al., "Feeding a Diet Containing a Fructooligosaccharide Mix Can Enhance *Salmonella* Vaccine Efficacy in Mice", Journal of Nutrition, Nutritional Immunology, American Society for Nutrition, 2008, pp. 123-129 (7 pages).

Boards of Appeal Of the European Patent Office Communication T0918/05 issued in European Application No. 99941588.8 dated Mar. 3, 2009.

Bode, Lars, "Recent Advances on Structure, Metabolism, and Function of Human Milk Oligosaccharides", The Journal of Nutrition: Recent Advances in Nutritional Sciences, 2006, vol. 136, pp. 2127-2130 (4 pages).

Carver, Jane D, "Advances in nutritional modifications of infant formulas", The American Journal of Clinical Nutrition, 2003, vol. 77(suppl), pp. 1550S-1554S (5 pages).

Charlwood et al., "A detailed analysis of Neutral and Acidic Carbohydrates in Human Milk", Analytical Biochemistry, 1999, vol. 273, pp. 261-277 (17 pages).

Claud et al., "Hypothesis: inappropriate colonization of the premature intestine can cause neonatal necrotizing enterocolitis", The FASEB Journal, Jun. 2001, vol. 15, No. 8, pp. 1398-1403 (6 pages).

Crittenden et al., "Production, properties and applications of food-grade oligosaccharides", Trends in Food Science & Technology, Nov. 1996, vol. 71, pp. 353-361 (9 pages).

Environ International Corporation, "Generally Recognized as Safe (GRAS) Determination for the Use of Galacto-Oligosaccharides (GOS) in Foods and Term Infant Formulas", Vivinal (R), pp. 1-iii, 1-4, Sep. 6, 2007 (8 pages).

Environ International Corporation, "GRAS Exemption Claim for Galacto-Gligosaccharides(GOS)" Friesland Foods Domo, Oct. 18, 2007, pp. 1-4 (9 pages).

Faldella et al., "The preterm infants antibody response to a combined diphtheria, tetanus, acellular pertussis and hepatitis B vaccine", Vaccine, 1998, vol. 16, No. 17, pp. 1646-1649 (4 pages).

Fanaro et al., "Galacto-oligosaccharides and long-chain fructo-oligosaccharides as prebiotics in infant formulas: A review", Acta Pediatrica, 2005, vol. 94 (Suppl 449), pp. 22-26 (6 pages).

Grollman et al. "Biosynthesis of Fucosyllactose and Other Oligosaccharides Found in Milk", The Journal of Biological Chemistry, vol. 240, No. 3, Mar. 1965 (7 pages).

Haug et al., "Bovine milk in human nutrition—a review", Lipids in Health and Disease, vol. 6, No. 25, pp. 1-16, Sep. 25, 2007 (16 pages).

Hesseling et al., "Consensus statement on the revised World Health Organization recommendations for BCG vaccination in HIV-infected infants", Int J Tuberc Lung Dis, 2008, vol. 12, No. 12, pp. 1376-1379 (4 pages).

Interlocutory decision in oppositions proceedings (Art. 101(3)(a) and 106(2) EPC) issued in European Application No. 04 077 394.7 dated Jul. 20, 2012 (21 pages).

International Search Report for PCT/NL2010/050446 dated Oct. 19, 2010 (5 pages).

International Search Report for PCT/NL2010/050447 dated Oct. 19, 2010 (5 pages).

Kidd, Parris, "Th1/Th2 Balance: The Hypothesis, its Limitations, and Implications for Health and Disease", Alternative Medicine Review, 2003, vol. 8, No. 3, pp. 223-246 (24 pages).

Kohlhuber et al., "Breastfeeding rates and duration in Germany: a Bavarian cohort study", British Journal of Nutrition, May 2008, vol. 99, No. 5, pp. 1127-1132, (6 pages).

Kovarik et al., "Optimization of vaccine responses in early life: The role of delivery systems and immunomodulatos", Immunology and Cell Biology, 1998, vol. 76, pp. 222-236 ( 15 pages).

Krathwohl et al., "Chemokine CXCL 10 (IP-10) is sufficient to trigger an immune response to injected antigens in a mouse model," Vaccine, vol. 24, 2006 pp. 2987-2993 (7 pages).

Minna-Maija et al., "Fecal Microflora in Healthy Infants Born by Different Methods of Delivery: Permanent Changes in Intestinal Flora after Cesarean Delivery", Journal of Pediatric Gastroenterology & Nutrition, Jan. 1999, vol. 28, No. 1, pp. 19-25 (13 pages).

Mitoulas et al., "Variation in fat, lactose and protein in human milk over 24h and througout the first year of lactation", British Journal of Nutrition, 2002, vol. 88, pp. 29-37 (9 pages).

Morrow et al., "Human-Milk Glycans That Inhibit Pathogen Binding Protect Breast-Feeding Infants against Infectious Diarrhea", The Journal of Nutrition, American Society for Nutritional Sciences, 2005, vol. 135, No. 5, pp. 1304-1307 (4 pages).

Nakamura et al., "The Milk Oligosaccharides of Domestic Farm Animals", Trends in Glycoscience and Glycotechnology, Mar. 2004, vol. 16, No. 88, pp. 135-142 (8 pages).

Newburg et al., "Innate protection conferred by fucosylated oligosaccharides of human milk against diarrhea in breastfed infants", Glycobiology, 2004, vol. 14, No. 3, pp. 253-263 (11 pages).

Newburg et al., "Neonatal protection by an innate immune system of human milk consisting of oligosaccharides and glycans", Journal of Animal Science, 2009, vol. 87, pp. 26-34 (11 pages).

Ninonuevo et al., "Infant Formula Oligosaccharides Opening the Gates (for Speculation)", Pediatric Research, 2008, vol. 64, No. 1, pp. 8-10 (3 pages).

Nittynen et al., "Galacto-oligosaccharides and bowel function", Scandinavian Journal of Food and Nutrition, 2007, vol. 51, No. 2, pp. 62-66 (5 pages).

Oftedal, Olav T., "Lactation in the Dog: Milk Composition and Intake by Puppies", The Journal of Nutrition, vol. 114, pp. 803-812, 1984 (10 pages).

Ruiz-Palacios et al., "Campylobacter jejuni Binds Intestinal H(O) Antigen (Fuca1, 2GalB1, 4GlcNAc), and Fucosyloligosaccharides

(56) References Cited

OTHER PUBLICATIONS of Human Milk Inhibit Its Binding and Infection", The Journal of Biological Chemistry, Apr. 18, 2003, vol. 278, No. 16, pp. 14112-14120 (9 pages).
Sotgiu et al., "Immunomodulation of fucosyl-lactose and lacto-N-fucopentaose on mononuclear cells from multiple sclerosis and healthy subjects", International Journal of Biomedical Science, Jun. 2006, vol. 2, No. 2, pp. 114-120 (7 pages).
Sotgiu et al., "Immunomodulation of fucosyl-lactose and lacto-N-fucopentaose on mononuclear cells from multiple sclerosis and healthy subjects",International Journal of Biomedical Science, vol. 2, No. 2, Jun. 15, 2006, pp. 114-120 (7 pages).
Sumiyoshi et al., "Determination of each neutral oligosaccharide in the milk of Japanese women during the course of lactation", British Journal of Nutrition, Jan. 2003, vol. 89, No. 1, pp. 61-69 (9 pages).
Torres et al., "Galacto-Oligosaccharides: Production, Properties, Applications, and Significance as Prebiotics", Comprehensive Reviews in Food Science and Food Safety, 2010, vol. 9, pp. 438-454 (17 pages).
Urashima et al., "Chemical characterization of oligosaccharides in chimpanzee, bonobo, gorilla, orangutan, and siamang milk or colostrum", Glycobiology, vol. 19, No. 5, 2009, pp. 499-508 (10 pages).
Urashima et al., "Oligosaccharides of milk and colostrum in non-human mammals", Glycoconjugate Journal, 2001, vol. 18, pp. 357-371 (15 pages).
Vandenplas, Y., "Oligosaccharides in Infant Formula", British Journal of Nutrition, 2002, vol. 87, Suppl. 2, pp. S293-S296 (4 pages).
Vos et al., "A specific prebiotic oligosaccharide mixture stimulates delayed-type hypersensitivity in a murine influenza vaccination model", International Immunopharmacology, 2006, vol. 6, pp. 1277-1286 (10 pages).
Vos et al., "Dietary supplementation of neutral and acidic oligosaccharides enhances Th1-dependent vaccination responses in mice", Pediatric Allergy and Immunology, 2007, vol. 18, pp. 304-312 (9 pages).
Zoppi et al., "Diet and Antibody Response to Vaccinations in Health Infants", The Lancet, Jul. 2, 1983, pp. 11-14 (4 pages).

\* cited by examiner

FUCOSYLLACTOSE AS BREAST MILK IDENTICAL NON-DIGESTIBLE OLIGOSACCHARIDE WITH NEW FUNCTIONAL BENEFIT

CROSS-REFERENCE TO RELATED APPLICATIONS

This application is a Continuation of U.S. application Ser. No. 15/866,667, filed Jan. 10, 2018, which is a Continuation of U.S. patent application Ser. No. 14/869,436, filed Sep. 29, 2015, which is a Continuation of U.S. patent application Ser. No. 13/383,822, filed Mar. 28, 2012, which is the U.S. National Stage Application of PCT/NL2010/050447, filed Jul. 12, 2010; which claims the benefit of and priority to U.S. Provisional Patent Application No. 61/256,453, filed Oct. 30, 2009, and European Patent Application No. 09165485.5, filed Jul. 15, 2009; all of which are hereby incorporated by reference herein in their entireties.

FIELD OF THE INVENTION

The present invention relates to infant nutrition with non-digestible oligosaccharides, in particular to the use thereof for stimulating the immune system.

BACKGROUND OF THE INVENTION

Human milk fed infants have a lower incidence of infections, including viral infections, than formula fed infants. Many components in human milk, including immunoglobulins (such as IgA), interleukin (IL)-1, IL-6, IL-8, IL-10, interferon-γ (IFN-γ), immunocompetent cells, transforming growth factor-β (TGF-β), lactoferrin, nucleotides, and non-digestible oligosaccharides (NDO) are thought to be involved in protection against infection with enteric or respiratory pathogens. TGF-β and dietary nucleotides were found to be components which may be responsible for increase in natural killer cell activity.

NDO are a major constituent of human milk and are a major element of the innate immune system of human milk. Human NDO promote the growth of a beneficial microbiota dominated by bifidobacteria and lactobacilli. Some human NDO are also known to be able to prevent directly the adhesion of pathogens and toxins.

Human milk is the preferred food for infants. However, it is not always possible or desirable to breast feed an infant. In such cases infant formulae or follow on formulae are a good alternative. These formulae should have an optimal composition in order to mimic the beneficial effects of breast milk as close as possible.

WO 2007/067053 discloses infant formula comprising the plant-derived prebiotics inulin and galacturonic acid oligosaccharide and the from lactose synthesized prebiotic trans-galacto-oligosaccharide to reduce infections.

WO 2007/010084 discloses mannan-poly- and oligosaccharides for immune stimulation.

U.S. Pat. No. 6,576,251 discloses a carbohydrate mixture for dietetic foods administered by the enteral or parenteral route consisting of (a) monosaccharide(s), (b) oligosaccharide(s) (at most hexasaccharides) and (c) polysaccharide(s) (at least heptasaccharides), where the mixing ratio a, b, c, in respect of weight, is: alpha=1, b=40 to 1000, and c=1 to 50, and containing at least 1 weight percent of fucose occurring either freely and/or bound to an oligosaccharide and/or a polysaccharide. The carbohydrate mixture is said to have both a nutritional and a biological effect which is considerably greater than the corresponding action of the individual constituents.

EP 1 629 850 provides a method and composition for the treatment and/or prevention of respiratory tract infection and/or respiratory tract infection disease, said method comprising orally administering a composition to a mammal, said composition comprising a galactose containing indigestible oligosaccharide and at least 5 wt. % digestible galactose saccharide.

EP 2 072 052 relates to a composition suitable for use in the prevention of opportunistic infections in immune-compromised individuals comprising a probiotic and a fucosylated oligosaccharide selected from the group comprising 2'-fucosyllactose, 3'fucosyllactose, difucosyllactose, lacto-N-fucopentaose, lacto-N-fucohexaose, fucosyllacto-N-hexaose and fucosyllacto-N-neohexaose. The document further discloses the use of such a composition in the prevention of opportunistic infections in immune-compromised individuals.

SUMMARY OF THE INVENTION

Human milk differs from milk from domestic animals in that it comprises more NDO and in that the NDO are structurally different. The group of human NDO is very complex, since it represents a heterogenic group of more than 130 different compounds with diverse sugar composition. Because of their complex and polymorphic structure, large-scale synthesis is complicated. It is therefore not yet technically and economically feasible to prepare infant nutrition with an NDO composition identical to human milk.

Recently, new techniques have become available to chemically synthesise specific types of NDO identical to specific human NDO, thereby offering the opportunity to test the immunomodulatory capacity of specific human NDO in in vitro and in vivo assays.

The inventors unexpectedly have found that fucosyllactose (FL), an oligosaccharide abundantly present in human breast milk and with a relatively simple structure, specifically increases the number and thereby the activity of Natural Killer (NK) cells. NK cells play an important role in the natural defence against viral infections and tumour cells. The finding which specific oligosaccharide is responsible for increasing NK cell activity now enables the design of nutritional compositions comprising FL, more particularly 2'-FL, for the use of increasing NK cells and/or NK cell activity.

DETAILED DESCRIPTION

The present invention thus concerns a method for stimulating NK cell activity and/or NK cell proliferation in a subject, said method comprising administering a composition comprising fucosyllactose to said subject, said composition not being human milk. In one embodiment the present method is a non-medical method for stimulating NK cell activity and/or NK cell proliferation in a subject. In one embodiment the present method is for treating and/or preventing viral infections in a subject.

The present invention also concerns a method for treating and/or preventing viral infections in a subject, said method comprising administering a composition comprising fucosyllactose to said subject, said composition not being human milk.

The invention can also be worded as the use of fucosyllactose in the manufacture of a composition for stimulating NK cell activity and/or NK cell proliferation, said composition not being human milk. In one embodiment the composition is for treating and/or preventing viral infections.

The invention can also be worded as the use of fucosyllactose in the manufacture of a composition for treating and/or preventing viral infections, said composition not being human milk.

The invention can also be worded as a composition comprising fucosyllactose for stimulating, in particular for use in stimulating, NK cell activity and/or NK cell proliferation, said composition not being human milk. In one embodiment the composition is for use in treating and/or preventing, viral infections.

The invention can also be worded as a composition comprising fucosyllactose for treating and/or preventing, in particular for use in treating and/or preventing, viral infections, said composition not being human milk.

The invention also concerns a method for treating and/or preventing infections, by stimulating natural killer (NK) cell activity and/or NK cell proliferation, said method comprising administering a composition comprising fucosyllactose to said subject, said composition not being human milk.

The invention can also be worded as the use of fucosyllactose in the manufacture of an enteral composition for treating and/or preventing infections, by stimulating natural killer (NK) cell activity and/or NK cell proliferation, said composition not being human milk.

The invention can also be worded as a composition comprising fucosyllactose for treating and/or preventing infections, in particular for use in and/or preventing infections, by stimulating natural killer (NK) cell activity and/or NK cell proliferation, said composition not being human milk.

The invention also concerns a method for enhancing vaccination response, said method comprising administering a composition comprising fucosyllactose to said subject, said composition not being human milk. In one embodiment the method is for enhancing vaccination response to vaccination with viral antigens.

The invention can also be worded as the use of fucosyllactose in the manufacture of an enteral composition for enhancing vaccination response. In one embodiment the composition is for enhancing vaccination response to vaccination with viral antigens.

The invention can also be worded as a composition comprising fucosyllactose for enhancing, in particular for use in enhancing, vaccination response. In one embodiment the composition is for enhancing vaccination response to vaccination with viral antigens.

The composition that is administered according to the present method, or that is used according to the present invention, is preferably enterally administered, more preferably orally. Or in other words the composition is preferably for enteral, preferably oral administration or in other words the composition is an enteral, preferably oral, composition.

Fucosyllactose

The present composition comprises fucosyllactose. Fucosyllactose (FL) is a non-digestible oligosaccharide present in human milk. It is not present in bovine milk. It consists of three monose units, fucose, galactose and glucose linked together. Galactose linked to glucose via a beta 1→4 linkage is called lactose. A fucose unit is linked to a galactose unit of a lactose via an alpha 1,2 linkage (2'-fucosyllactose, 2'-FL) or to the glucose unit of lactose via an alpha 1,3 linkage (3-fucosyllactose, 3-FL). The present composition preferably comprises 2'-FL.

2'-FL, preferably α-L-Fuc-(1→2)-β-D-Gal-(1→4)-D-Glc, and 3-FL, preferably α-L-Fuc-(1→3)-[β-D-Gal-(1→4)]-D-Glc), are commercially available for instance from Sigma-Aldrich. Alternatively, they can be isolated from human milk, for example as described in Andersson & Donald, 1981, J Chromatogr. 211:170-1744, or produced by genetically modified micro-organisms, for example as described in Albermann et al, 2001, Carbohydrate Res. 334:97-103.

Preferably, the composition comprises 1 mg to 3 g fucosyllactose per 100 ml, more preferably 10 mg to 2 g, even more preferably 20 mg to 100 mg FL per 100 ml. Based on dry weight, the composition preferably comprises 0.007 wt % to 20 wt % fucosyllactose, more preferably 0.07 wt % to 10 wt %, even more preferably 0.15 wt % to 1 wt %. A lower amount of fucosyllactose will be less effective in increasing NK cells and/or increasing NK cell activity, whereas a too high amount will result in unnecessary high costs of the product.

Non-Digestible Oligosaccharides Other than FL

The present composition preferably comprises non-digestible oligosaccharides (NDO) other than FL. Preferably the NDO other than FL stimulate the growth of bifidobacteria and/or lactobacilli, more preferably bifidobacteria. An increased content of bifidobacteria and/or lactobacilli stimulate the formation of a healthy intestinal microbiota. The NDO are preferably not or only partially digested in the intestine by the action of acids or digestive enzymes present in the human upper digestive tract, in particular in the small intestine and stomach, and are fermented by the human intestinal microbiota. For example, sucrose, lactose, maltose and the common maltodextrins are considered digestible.

Preferably the present composition comprises non-digestible oligosaccharides with a DP in the range of 2 to 250, more preferably 2 to 60. The non-digestible oligosaccharide is preferably at least one, more preferably at least two, preferably at least three selected from the group consisting of fructo-oligosaccharides, galacto-oligosaccharides, xylo-oligosaccharides, arabino-oligosaccharides, arabinogalacto-oligosaccharides, gluco-oligosaccharides, chito-oligosaccharides, glucomanno-oligosaccharides, galactomanno-oligosaccharides, mannan-oligosaccharides, sialic acid comprising oligosaccharides, and uronic acid oligosaccharides. The group of fructo-oligosaccharides includes inulins, the group of galacto-oligosaccharides includes transgalacto-oligosaccharides or beta-galacto-oligosaccharides, the group of gluco-oligosaccharides includes cyclodextrins, gentio- and nigero-oligosaccharides and non-digestible polydextrose, the group of galactomanno-oligosaccharides includes partially hydrolyzed guar gum, and the group of uronic acid oligosaccharides includes galacturonic acid oligosaccharides and pectin degradation products.

More preferably the present composition comprises at least one, more preferably at least two, most preferably three selected from the group consisting of fructo-oligosaccharides, beta-galacto-oligosaccharides and uronic acid oligosaccharides. More preferably the composition comprises beta-galacto-oligosaccharides.

In a preferred embodiment the composition comprises a mixture of inulin and short chain fructo-oligosaccharides. In a preferred embodiment the composition comprises a mixture of galacto-oligosaccharides and fructo-oligosaccharides selected from the group consisting of short chain fructo-oligosaccharides and inulin, more preferably inulin. A mixture of at least two different non-digestible oligosaccharides advantageously stimulates the beneficial bacteria of the intestinal microbiota to a greater extent. Preferably the weight ratio in a mixture of the two different non-digestible oligosaccharides, preferably galacto-oligosaccharides and fructo-oligosaccharide, is between 25 and 0.05, more preferably between 20 and 1. Galacto-oligosaccharides, preferably beta-galacto-oligosaccharides, are more capable of stimulating bifidobacteria. Preferably the present composition comprises galacto-oligosaccharides, preferably beta-galacto-oligosaccharides, with a degree of polymerization (DP) of 2 to 10 and/or fructo-oligosaccharides with a DP of 2 to 60.

The galacto-oligosaccharides preferably are beta-galacto-oligosaccharides. In a particularly preferred embodiment the present composition comprises beta-galacto-oligosaccharides ([galactose]n-glucose; wherein n is an integer ranging from 2 to 60, i.e. 2, 3, 4, 5, 6, . . . , 59, 60; preferably n is selected from 2, 3, 4, 5, 6, 7, 8, 9, and 10), wherein the galactose units are in majority linked together via a beta linkage. Beta-galacto-oligosaccharides are also referred to as trans-galacto-oligosaccharides (TOS). Beta-galacto-oligosaccharides are for example sold under the trademark Vivinal™ (Borculo Domo Ingredients, Netherlands). Another suitable source is Bi2Munno (Classado). Preferably the TOS comprises at least 80% beta-1,4 and beta-1,6 linkages based on total linkages, more preferably at least 90%.

Fructo-oligosaccharide is a NDO comprising a chain of beta-linked fructose units with a DP or average DP of 2 to 250, more preferably 2 to 100, even more preferably 10 to 60. Fructo-oligosaccharide includes inulin, levan and/or a mixed type of polyfructan. An especially preferred fructo-oligosaccharide is inulin. Fructo-oligosaccharide suitable for use in the compositions is also commercially available, e.g. Raftiline® HP (Orafti). Preferably the fructo-oligosaccharide has an average DP above 20.

Uronic acid oligosaccharides are preferably obtained from pectin degradation products. Hence the present composition preferably comprises a pectin degradation product with a DP of 2 to 100. Preferably the pectin degradation product is prepared from apple pectin, beet pectin and/or citrus pectin. Preferably the uronic acid oligosaccharide is a galacturonic acid oligosaccharide. Preferably the composition comprises FL and one of the group selected from galacto-oligosaccharide and uronic acid oligosaccharide.

Besides FL, most preferably the composition comprises beta-galacto-oligosaccharide, fructo-oligosaccharide and a uronic acid oligosaccharide. It was found that such a combination acts synergistically with fucosyllactose, in particular 2'-fucosyllactose. The weight ratio beta-galacto-oligosaccharide:fructo-oligosaccharide:uronic acid oligosaccharide is preferably (20 to 2):1:(1 to 20), more preferably (20 to 2):1:(1 to 10), even more preferably (20 to 2):1:(1 to 3), even more preferably (12 to 7):1:(1 to 2). Most preferably the weight ratio is about 9:1:1.1. Preferably the weight ratio FL to beta-galacto-oligosaccharide, preferably TOS, is from 5 to 0.05, more preferably 5 to 0.1, more preferably from 2 to 0.1. Preferably the weight ratio FL to fructo-oligosaccharide, preferably inulin, is from 10 to 0.05, more preferably 10 to 0.1, more preferably from 2 to 0.5. Preferably the weight ratio FL to uronic acid oligosaccharide, preferably derived from pectin, is from 10 to 0.05, more preferably 10 to 0.1 more preferably from 2 to 0.5.

Preferably, the composition comprises 80 mg to 4 g non-digestible oligosaccharides, including fucosyllactose, per 100 ml, more preferably 150 mg to 2 g, even more preferably 300 mg to 1 g non-digestible oligosaccharides per 100 ml. Based on dry weight, the composition preferably comprises 0.25 wt % to 25 wt % non-digestible oligosaccharides including fucosyllactose, more preferably 0.5 wt % to 10 wt %, even more preferably 1.5 wt % to 7.5 wt %. A lower amount of non-digestible oligosaccharides will be less effective in stimulating the beneficial bacteria in the microbiota, whereas a too high amount will result in side-effects of bloating and abdominal discomfort.

Nutritional Composition

Preferably the composition comprising fucosyllactose is a nutritional composition. The composition of the present invention is not human milk. The present composition is preferably enterally administered, more preferably orally.

The present composition is preferably a nutritional formula, preferably an infant formula. The present composition can be advantageously applied as a complete nutrition for infants. The present composition preferably comprises a lipid component, protein component and carbohydrate component and is preferably administered in liquid form. The present invention includes dry food, preferably a powder, which is accompanied with instructions as to admix said dry food mixture with a suitable liquid, preferably with water.

The present invention advantageously provides a composition wherein the lipid component provides 5 to 50% of the total calories, the protein component provides 5 to 50% of the total calories, and the digestible carbohydrate component provides 15 to 85% of the total calories. The present invention advantageously provides a composition wherein the lipid component provides 20 to 50% of the total calories, the protein component provides 5 to 30% of the total calories, and the digestible carbohydrate component provides 30 to 70% of the total calories. Preferably, in the present composition the lipid component provides 35 to 50% of the total calories, the protein component provides 7.5 to 12.5% of the total calories, and the digestible carbohydrate component provides 40 to 55% of the total calories. For calculation of the % of total calories for the protein component, the total of energy provided by the proteins, peptides and amino acids needs to be taken into account.

The present composition preferably comprises at least one lipid selected from the group consisting of animal lipid, excluding human lipids, and vegetable lipids. Preferably the present composition comprises a combination of vegetable lipids and at least one oil selected from the group consisting of fish oil, animal oil, algae oil, fungal oil, and bacterial oil. The present composition preferably comprises long chain poly-unsaturated fatty acids (LC-PUFA). LC-PUFA are fatty acids or fatty acyl chains with a length of 20 to 24 carbon atoms, preferably 20 or 22 carbon atoms comprising two or more unsaturated bonds. More preferably the present composition comprises eicosapentaenoic acid (EPA, n-3), docosahexaenoic acid (DHA, n-3) and/or arachidonic acid (ARA, n-6).

Preferably the present composition comprises at least 0.1 wt. %, preferably at least 0.25 wt. %, more preferably at least 0.6 wt. %, even more preferably at least 0.75 wt. % LC-PUFA with 20 and 22 carbon atoms based on total fat content.

The content of LC-PUFA, particularly the LC-PUFA with 20 and 22 carbon atoms, preferably does not exceed 6 wt %, more preferably does not exceed 3 wt. % of the total fat content as it is desirable to mimic human milk as closely as possible. The LC-PUFA may be provided as free fatty acids, in triglyceride form, in diglyceride form, in monoglyceride form, in phospholipid form, or as a mixture of one or more of the above. The present composition preferably comprises between 5 and 75 wt. % polyunsaturated fatty acids based on total fat, preferably between 10 and 50 wt. %.

The protein used in the nutritional composition is preferably selected from the group consisting of non-human animal proteins (preferably milk proteins), vegetable proteins (preferably soy protein and/or rice protein), hydrolysates thereof, free amino acids and mixtures thereof. The present composition preferably contains casein, whey, hydrolyzed casein and/or hydrolyzed whey protein. Preferably the protein comprises intact proteins, more preferably intact bovine whey proteins and/or intact bovine casein proteins.

The present composition preferably contains digestible carbohydrates selected from the group consisting of sucrose, lactose, glucose, fructose, corn syrup solids, starch and maltodextrins, more preferably lactose.

In view of the above, it is also important that the liquid food does not have an excessive caloric density, however still provides sufficient calories to feed the subject. Hence, the liquid food preferably has a caloric density between 0.1 and 2.5 kcal/ml, even more preferably a caloric density of between 0.5 and 1.5 kcal/ml, most preferably between 0.6 and 0.8 kcal/ml.

Preferably the present composition comprises nucleotides and/or nucleosides, more preferably nucleotides. Preferably, the composition comprises cytidine 5'-monophospate, uridine 5'-monophospate, adenosine 5'-monophospate, guanosine 5'-monophospate, and/or inosine 5'-monophospate, more preferably cytidine 5'-monophospate, uridine 5'-monophospate, adenosine 5'-monophospate, guanosine 5'-monophospate, and inosine 5'-monophospate. Preferably the composition comprises 5 to 100, more preferably 5 to 50 mg, most preferably 10 to 50 mg nucleotides and/or nucleosides per 100 gram dry weight of the composition. The presence of nucleotides and/or nucleotides advantageously stimulates NK cell activity. The nucleotides and/or nucleosides are deemed to act synergistically with the fucosyllactose of the present composition.

Application

In one embodiment the present composition is used for stimulating natural killer cell activity and/or natural killer cell proliferation. In one embodiment the present composition is used for treating and/or preventing viral infections. In one embodiment the composition for stimulating natural killer cell activity and/or natural killer cell proliferation, and/or for treating and/or preventing viral infections is for administering to HIV patients, elderly and/or oncology patients.

NK cells are a type of cytotoxic lymphocytes that constitute a major component of the innate immune system. NK cells play a major role in defense against intracellular infections. NK-cells are defined as large granular lymphocytes that do not express T-cell antigen receptors (TCR) or Pan T marker CD3 or surface immunoglobulins (Ig) B cell receptor but that usually express the surface markers CD16 (FcγRIII) and CD56 in humans. They were named "natural killers" because of the initial notion that they do not require activation in order to kill cells that are missing "self" markers of major histocompatibility complex (MHC) class I. NK cells have two major types of effector function; cell killing and the secretion of cytokines. Increasing NK cell activity (by increasing the number of NK cells and/or by increasing the specific activity of an NK cell), results in an increased resistance against viral infections. The use of a nutritional composition comprising fucosyllactose is therefore preferably for preventing and/or treating viral infections, more preferably viral infections caused by orthomyxoviridae, in particular the influenza virus, herpesviridae, rotavirus, cytomegalovirus, caliciviridae, respiratory syncytial virus, human imunodeficiency virus and/or rhinovirus. The use of a nutritional composition comprising fucosyllactose is therefore preferably for preventing and/or treating viral infections, more preferably the viral infections common cold, flu, measles, chicken pox, viral diarrhoea, viral gastro-enteritis, HIV infection and/or viral respiratory tract infections. In a preferred embodiment the present invention is used for HIV patients. In one embodiment, the present invention concerns providing nutrition to a HIV patient. The present composition is advantageous for HIV patients since HIV patients have a decreased natural killer cell activity.

The use of a nutritional composition comprising fucosyllactose is therefore especially beneficial for infant formula. In one embodiment, the present invention concerns providing nutrition to an infant. Formula fed infants have an underdeveloped immune system compared with adults and are more prone to viral infections than human milk fed infants. Preferably the infant is from 0 to 36 months of age, more preferably of 0 to 18 months, even more preferably of 0 to 12 months, most preferably of 0 to 6 months of age. The younger the infant is, the less developed the immune system.

The composition comprising fucosyllactose even more advantageously is used in preterm infants and/or very low or low birth weight infants, since these infants are even more vulnerable and/or prone to viral infections.

The composition comprising fucosyllactose even more advantageously is used in infants delivered via Caesarean section. Caesarean section born infants are born in a hospital in an environment having more pathogens against which the antibodies, conferred by the mother to the infant, are not effective against. Caesarean section born infants have a delayed and less optimal colonization of the large intestinal tract and therefore are also more prone to intestinal infections.

The composition comprising fucosyllactose is advantageously used for nutrition for elderly. In one embodiment, the present invention concerns providing nutrition to an elderly person. An elderly person is a person having an age of 55 years or more, in particular of the age of 65 or more. Elderly have a demonstrated lower activity of natural killer cell activity than healthy young adult individuals. Elderly are especially vulnerable to viral infection complications. In a preferred embodiment the present invention is used for treatment and/or prevention of immunosenescence in elderly. Elderly are more prone to the development of tumours. NK cell activity suppresses tumour cell proliferation. In a preferred embodiment the present invention is used for nutrition in cancer patients. Oncology patients have a lower natural killer cell activity than healthy young adult individuals.

EXAMPLES

Example 1

Materials and Methods 6-8 Weeks old female C57BL/6 mice (Charles River) received semi-purified AIN-93G-based diets (Research Diet Service, Wijk bij Duurstede, the Netherlands), comprising 1) 2 wt % beta-galacto-oligosaccharide (GOS; source Vivinal GOS, Borculo Domo), fructo-oligosaccharide (FOS; source RaftilineHP, Orafti) and galacturonic acid oligosaccharide (Source AOS) in a 9:1:1.1 ratio. AOS are produced from pectin (Stidzucker AG, Mannheim, Germany), with a DP of 1-20. It consists of approximately 75% galacturonic acid oligomers, based on total weight;

2) 1 wt % lactoneotetraose (LNnT), 3) 1 wt % 3'-sialyl lactose (3'-SL), or 4) 1 wt % 2'-fucosyllactose (2'-FL).

All groups were compared to the unsupplemented control diet. Dietary supplementation started 14 days before the first vaccination and lasted until the end of the experiment, 31 days after the first vaccination.

Vaccination experiments were performed using Influvac (Solvay Pharmaceuticals, Weesp, the Netherlands) from season 2005/2006. The mice received a primary vaccination and a booster vaccination, consisting of a subcutaneous (sc) injection of a 1:1 mix of vaccine and adjuvant in a total volume of 100 µl. The booster vaccination was given at 21 days after the primary vaccination. The experiments ended 10 days after booster vaccination. Blood samples were taken at the end of the experiment. Negative control groups that were included received injections with a 1:1 mix of PBS and adjuvant in a total volume of 100 µl. To determine the percentage of NK cells, cells were labelled with FITC-labelled anti-mouse CD3 mAb in combination with PE-labelled anti-mouse NK1.1 mAb. NK cell cytotoxicity in spleen cell suspensions was assayed using standard $^{51}Cr$ release assays. Briefly, NK cell cytotoxicity was tested using YAC-1 target cells. The percentage of specific $^{51}Cr$ release was calculated as the percentage of specific lysis=(experimental release−spontaneous release)/(total detergent release−spontaneous release)×100. The spontaneous release values were always <15% of total lysis.

The percentage of regulatory T cells (Treg) was determined by flow cytometry (FACSCalibur) using allophycocyanin (APC-)labelled anti-mouse CD3 mAb, Pe-Cy5-labeled anti-mouse CD4 mAb and phycoerythrin (PE)-labelled anti-mouse CD25 mAb in combination with intracellular staining of fluorescein-isotiocyanate (FITC)-labelled Foxp3 mAb, according to the instructions offered by the manufactures (eBiosciences, San Diego, Calif.).

Statistical analysis was performed using GraphPadPrism software. Statistical differences between test and control groups were analysed by ANOVA and post hoc Dunnett's test if multiple groups were compared to a single (control) group. P-values<0.05 were considered significant in all experiments.

Results

The immunomodulatory effect of three chemically synthesised human oligosaccharides was compared with GOS/FOS/AOS. Supplementation with GOS/FOS/AOS, LNnT, 2'-FL or 3'-SL resulted in a significant increase of the DTH response, a TH1-dependent parameter, compared with control-fed animals.

Interestingly, the percentage of NK cells in the spleen was significantly increased in mice supplemented with human oligosaccharides compared to control and GOS/FOS/AOS-supplemented mice, see table 1. This effect was highest with 2'-FL. To examine whether the increase in the percentage of NK cells in human oligosaccharides-supplemented groups also correlated with functional activity, NK cell activity was measured in mouse splenocytes. A significant increased NK cell activity was detected in the splenocytes of mice that were supplemented with 2'-FL compared to controls, see Table 1.

TABLE 1

Effect of dietary NDO similar to human milk NDO on NK cells and NK cell activity.

| Dietary intervention | % NK 1.1 + cells (SE) | NK cell activity, % lysis At E:T ratio 1:50 |
|---|---|---|
| Sham control | 2.5 (0.2) | 1.57 |
| Control | 2.2 (0.1) | 1.13 |
| GOS/FOS/AOS | 2.5 (0.1) | 1.95 |
| LNnT | 2.8 (0.1)* | 2.14 |
| 3'-SL | 3.0 (0.2)* | 1.93 |
| 2'-FL | 3.7 (0.1)** | 2.48* |

*indicates $p < 0.05$ compared to control group
**indicates $p < 0.01$ compared to control group Finally, the amount of regulatory T cells (Treg) was decreased to the highest extent with the diet with FL as can be seen in Table 2.

TABLE 2

Effect of dietary NDO similar to human milk NDO on percentage of regulatory T cells Treg.

| Dietary intervention | Treg percentage (s.e.m.) |
|---|---|
| Sham control | 3.6 (0.4) |
| Control | 3.9 (0.2) |
| GOS/FOS/AOS | 4.1 (0.3) |
| LNnT | 3.2 (0.2) |
| 3'-SL | 2.8 (0.2)* |
| 2'-FL | 2.8 (0.2)* |

*indicates $p < 0.05$ compared to control group

The decrease in regulatory T cells is indicative for a decreased inhibition of immune response and hence enables an increased vaccination response to the viral antigens. A temporarily decrease of regulatory T cells can be especially beneficial when vaccination is to occur.

Overall, these results support that oral supplementation with 2'-FL stimulates growth and/or activity of NK cells. These results are indicative for an effect of dietary 2'-FL for enhancing vaccination response, in particular vaccination with viral antigens. These results are indicative for an effect of dietary 2'-FL for treating and/or preventing viral infections.

Example 2

Infant formula for stimulating NK cell activity comprising per 100 ml (13.9 dry weight):

1.4 g protein (whey and casein)

7.3 g digestible carbohydrates (including lactose)

3.6 g fat (vegetable fat, fish oil)

0.8 g non-digestible oligosaccharides of which 80 mg 2'-fucosyllactose and 640 mg beta-galacto-oligosaccharides, and 80 mg fructo-oligosaccharides Further are included: choline, myo-inositol, taurine, minerals, trace elements, and vitamins as known in the art.

Example 3

A preferred composition that can be used for the stimulation of natural killer cell activity in HIV patients may comprise per 100 g dry weight.

| | |
|---|---|
| Dietary fiber | 5-50 g |
| Fructo-oligosaccharide | 5% of total dietary fibre |
| Galacto-oligosaccharide | 40% of total dietary fiber |
| Pectin hydrolysate | 50% of total dietary fiber |
| 2'-FL | 5% f total dietary fiber |
| N-acetyl cysteine | 0.5-5 g |
| Carbohydrate (not dietary fiber) | 2-20 g |
| Fat | 4-20 g |

What is claimed is:

1. A method for treating viral diarrhea caused by rotavirus, comprising administering to a subject in need thereof a composition comprising 1 mg to 3 g per 100 ml composition of 2' fucosyllactose,
wherein the composition is not human milk, and wherein the administration stimulates natural killer cell activity and/or natural killer cell proliferation.

2. The method according to claim 1, wherein the subject is an infant, a HIV patient, an elderly person, and/or an oncology patient.

3. The method according to claim 1, wherein the subject is a preterm infant and/or a very low or low birth weight infant.

4. The method according to claim 1, wherein the subject is an infant delivered via Caesarean section.

5. The method according to claim 1, wherein the composition additionally comprises at least one of beta-galacto-oligosaccharides, fructo-oligosaccharides and uronic acid oligosaccharides.

6. The method according to claim 1, wherein the composition additionally comprises beta-galacto-oligosaccharides.

7. The method according to claim 1, wherein the composition additionally comprises long chain poly-unsaturated fatty acids (LC-PUFA) with a length of 20 or 22 carbon atoms comprising two or more unsaturated bonds.

8. The method according to claim 1, wherein the composition additionally comprises nucleotides and/or nucleosides.

9. The method according to claim 8, wherein the composition additionally comprises nucleotides.

10. The method according to claim 1, wherein the composition comprises 0.07 to 1 wt % fucosyllactose, based on dry weight of the composition.

11. The method according to claim 1, wherein the composition comprises 5 to 50% protein, 15 to 85% digestible carbohydrates, and 5 to 50% fat, based on total energy.

* * * * *